US00PP17936P3

(12) United States Plant Patent

Morris, Jr.

(10) Patent No.: US PP17,936 P3

(45) Date of Patent: Aug. 21, 2007

(54) *VIBURNUM* PLANT NAMED 'VERNON MORRIS'

(50) Latin Name: *Viburnum dilatatum*
Varietal Denomination: Vernon Morris

(75) Inventor: Vernon R. Morris, Jr., Sebring, FL (US)

(73) Assignee: CP Delaware, Inc., Wilmington, DE (US)

( * ) Notice: Subject to any disclaimer, the term of this patent is extended or adjusted under 35 U.S.C. 154(b) by 15 days.

(21) Appl. No.: 11/311,410

(22) Filed: Dec. 20, 2005

(65) Prior Publication Data

US 2007/0143892 P1 Jun. 21, 2007

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
*Assistant Examiner*—Annette H Para
(74) *Attorney, Agent, or Firm*—Buchanan Ingersoll & Rooney PC

(57) ABSTRACT

The new *Viburnum dilatatum* cultivar is provided that was discovered as a chance seedling of unknown parentage. The plant displays an upright and rounded configuration. The plant is freely branching and forms a dense and bushy growth habit. The attractive medium green foliage is relatively less susceptible to marginal scorching than other plants of the species. Attractive white flowers are formed in large hemispherical cymes. The attractive large creamy-yellow fruit persists until later spring. The new cultivar is well suited to provide colorful ornamentation in gardens and in the landscape over an extended period of time.

3 Drawing Sheets

Botanical/commercial classification: *Veburnum dilataum*/*Viburnum* Plant.
Varietal denomination: cv. Vernon Morris.

SUMMARY OF THE INVENTION

*Viburnum* plants are recognized to be a varied and diversified group of shrubs that are widely grown to provide ornamentation. They are appreciated for their white, cream, and sometimes pink spring flowers, good foliage, interesting shape, and colored fruit that attracts birds.

The new and distinct Linden *Viburnum* (i.e., *Viburnum dilatatum*) plant originated as a chance seedling that was discovered while growing among plants in my yard at Pottstown, Pa., U.S.A. The parentage of the new cultivar is unknown. It was likely the result of an open-pollinated cross between unnamed and non-patented *Viburnum dilatatum* plants growing on my property. I was primarily attracted to the new cultivar in view of its attractive large uniquely colored berry set. The new plant was discovered and selected during the spring of 1993.

It was found that the new *Viburnum dilatatum* plant of the present invention possesses the following combination of characteristics:

(a) displays an upright and rounded configuration, (b) is freely branching and forms a dense and bushy growth habit, (c) displays attractive durable medium green foliage that is relatively less susceptible to marginal scorching than other plants of this species, (d) forms numerous small white flowers in large hemispherical cymes, and (e) forms attractive large creamy-yellow fruit that persists until late spring.

When a side-by-side comparison of the new cultivar and the *Viburnum dilatatum* 'Erie' cultivar (non-patented in the United States) is made at Jennersville, Pa., U.S.A., the new cultivar can be readily distinguished. More specifically, the new cultivar is more upright and more freely branching with more durable foliage that is less susceptible to marginal scorching. The cymes of the new cultivar are rounded while those of 'Erie' cultivar tend to be flat-topped. Also, the fruits of the new cultivar are larger and creamy yellow in coloration whereas those of the 'Erie' cultivar are red in the summer changing to coral-pink in the winter.

When a side-by-side comparison of the new cultivar with the *Viburnum dilatatum* 'Michael Dodge' cultivar (non-patented in the United States) at the same location, a number of differences also are readily apparent. More specifically, the new cultivar also is more upright and more freely branching with more durable foliage that is less susceptible to marginal scorching. Instead of rounded cymes, the cymes of 'Michael Dodge' cultivar are flat-topped. Additionally, the fruit of 'Michael Dodge' cultivar is smaller and light green in coloration.

The new cultivar is well suited to provide attractive colorful ornamentation in gardens and in the landscape over an extended period of time.

Asexual reproduction of the new cultivar at Pottstown, Pa., U.S.A., beginning in 1994 by the rooting of softwood cuttings has demonstrated that the distinctive characteristics of the new cultivar of the present invention are reliably transmitted from one generation to another. Accordingly, the new cultivar reproduces in a true-to-type manner by such technique.

The new cultivar has been named 'Vernon Morris'.

BRIEF DESCRIPTION OF THE PHOTOGRAPHS

The accompanying photographs show as true as it is reasonably possible to make the same in color illustrations of this character typical specimens of the new cultivar of the present invention. The depicted plants were approximately four years of age and were growing outdoors under full sun at Jennersville, Pa., U.S.A.

DETAILED DESCRIPTION

Figure 1:
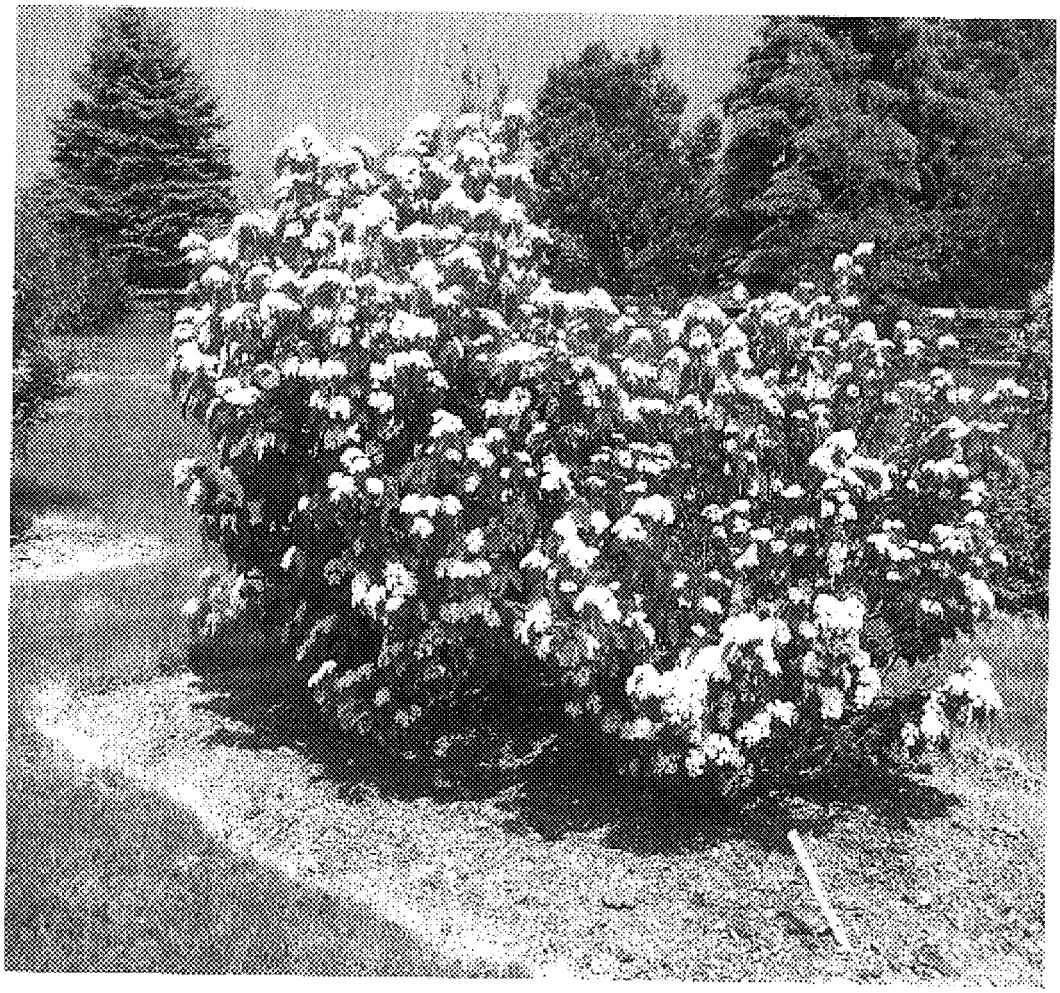
FIG. 1 shows a pair of flowering plants of the new cultivar while displaying a profusion white blossoms in large hemispherical cymes.
Figure 2:
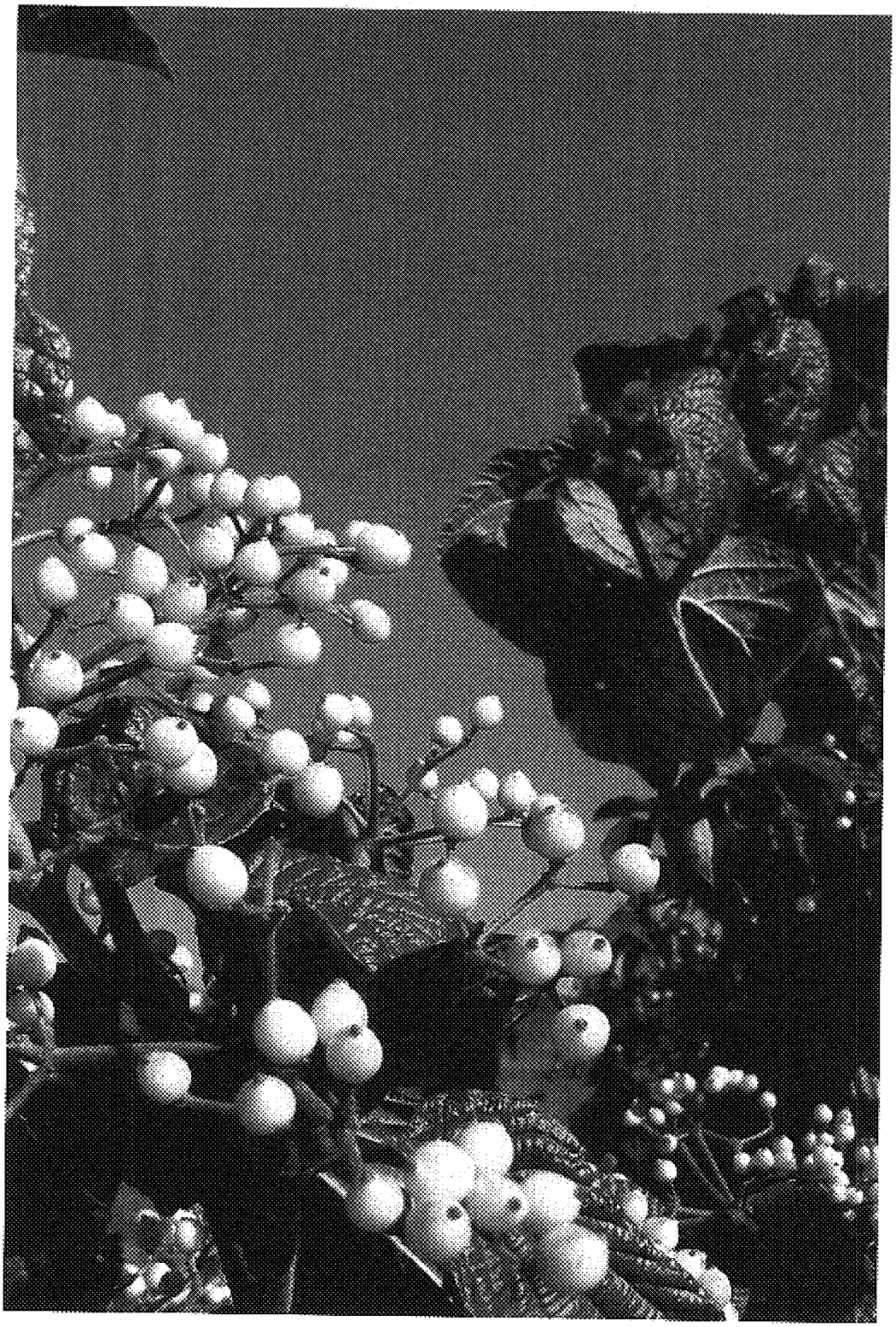
FIG. 2 shows a close view of the large creamy-yellow fruit of the new cultivar.
Figure 3:
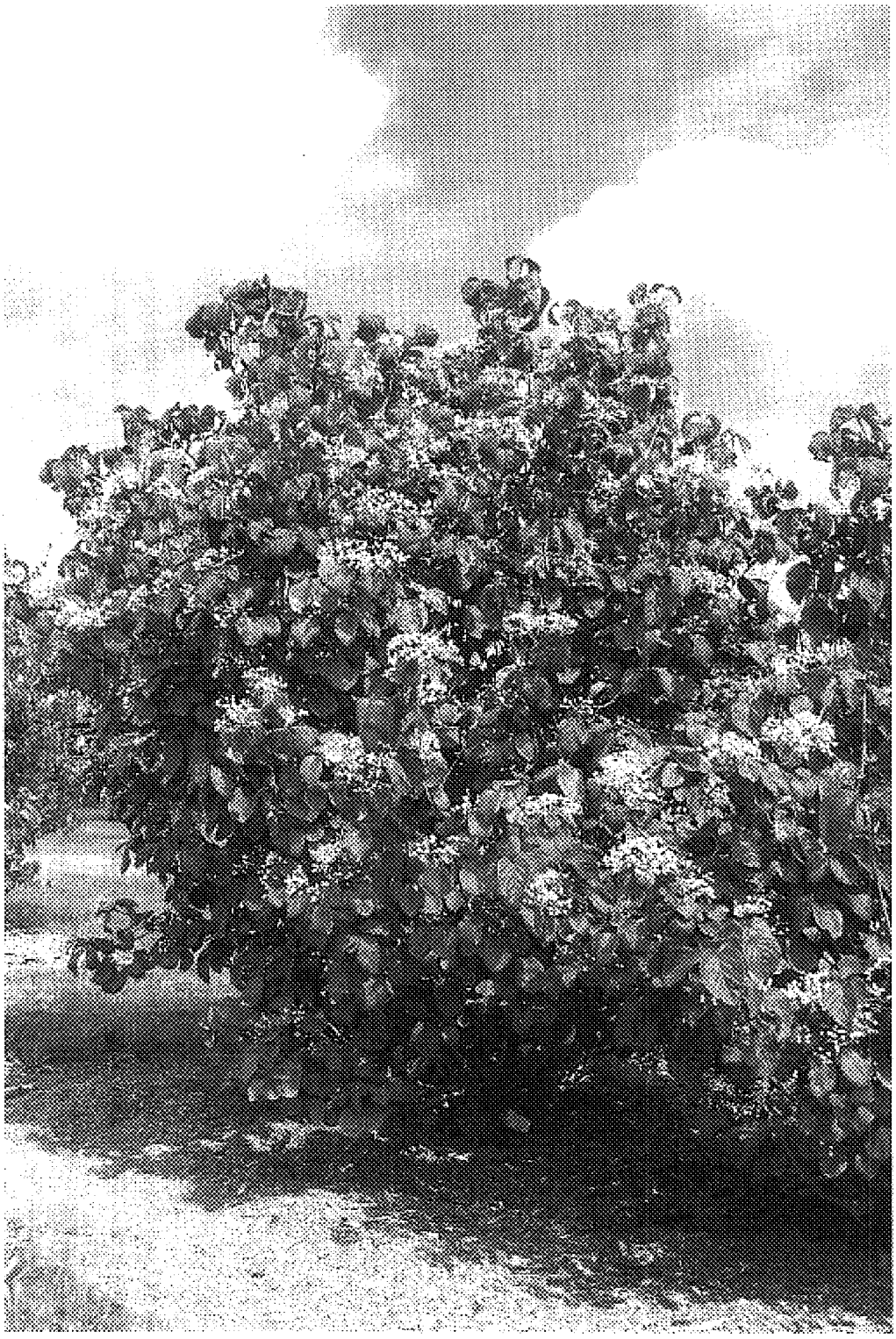
FIG. 3 shows an entire plant of the new cultivar with foliage and fruit set.

The following description is based upon the observation of mature plants of the new cultivar while growing in an outdoor garden in full sun at Jennersville, Pa., U.S.A. The chart used in the identification of the colors is the R.H.S. Colour Chart of the Royal Horticultural Society, London, England.

Plant:

*Height.*—Approximately 2 to 3 m.
*Width.*—Approximately 2 to 3 m.
*Growth habit.*—Upright and rounded, dense and bushy.
*Branching habit.*—Freely branching particularly when pinched.
*Branch number.*—Commonly approximately 32 lateral branches per plant when pinched.
*Branch length.*—Approximately 30 cm on average.
*Branch diameter.*—Approximately 7.5 mm on average.
*Internode length.*—Approximately 9.1 cm on average.
*Branch texture.*—Pubescent.
*Branch color.*—Grey-Brown Group 199C.
*Lenticels.*—Commonly less than 1 mm in diameter and Greyed-Yellow Group 161D in coloration.
*Roots.*—Fibrous with much branching.

Foliage:

*Arrangement.*—Opposite, with simple deciduous leaves.
*Quantity.*—Approximately 20 leaves per lateral branch on average.
*Mature length.*—Approximately 11 cm on average.
*Mature width.*—Approximately 8 cm at the widest point on average.
*Shape.*—Broadly ovate, generally symmetrical and relatively long persisting.
*Apex.*—Acute to obtuse.
*Base.*—Obtuse to rounded.
*Margin.*—Undulate.
*Texture.*—Pubescent and slightly rugose.
*Color.*—Young leaf: Upper Surface: Green Group 137B. Lower surface: Green Group 137C. Mature leaf: Upper Surface: Green Group 137B. Lower Surface: Green Group 137C. Venation: Greyed-green Group 193B.
*Stress tolerance.*—Relatively less susceptible to marginal scorching than other plants of the species.
*Petiole.*—Approximately 1 cm in length, approximately 5 mm in diameter, and Yellow Green Group 147B in coloration.

Inflorescence:

*Description.*—Small single rounded flowers arranged in rounded and hemispherical cymes.
*Flowering time.*—Commonly from May through June at Jennersville, Pa., U.S.A.
*Longevity.*—Approximately 4 weeks on the plant.
*Quantity.*—Freely-flowering. The number flowers per cyme commonly is approximately 250 with approximately 1 to 5 cymes per lateral branch.
*Calyx.*—Star-shaped, five-toothed, and near Green Group 141A in coloration.
*Sepals.*—Shape: With an acute apex and an entire margin. Size: Less than 1 mm in length and diameter. Color: Near Green Group 141A.
*Buds.*—Shape: ovate. Length: Approximately 1 cm. Diameter: Approximately 7.5 mm. Color: Near Green Group 141A.
*Cyme diameter.*—Approximately 10 cm.
*Cyme length.*—Approximately 6.5 cm.
*Petal number.*—Five fused petals in a single whorl.
*Petal shape.*—Obovate.
*Petal apex.*—Obtuse.
*Petal margin.*—Entire.
*Petal length.*—Approximately 4 mm.
*Petal width.*—Approximately 3 mm.
*Petal color.*—When opening White Group 155A on both surfaces, when fully open White Group 155D on both surfaces, and the changing to Greyed-Orange Group 177A with subsequent development.
*Stamen.*—Five in number.
*Anthers.*—Approximately less than 1 mm in size, and Yellow-Orange Group 22A in coloration.
*Pollen.*—Commonly formed in each flower in a sparse quantity, and Yellow-Orange Group 22A in coloration.
*Pistil.*—One per flower, and commonly less than about 1 mm in length.
*Style.*—Less than 1 mm in length.
*Stigma.*—Three-lobed and White Group 155A in coloration.
*Fragrance.*—None.
*Pedicels.*—Relatively strong, commonly borne at an angle of approximately 80 degrees from the vertical, approximately 5 to 25 mm in length and Green Group 141A in coloration.

Fruit:

*Shape.*—Broad ovate.
*Type.*—Drupe.
*Length.*—Approximately 7 mm.
*Diameter.*—Approximately 7 mm.
*Color.*—Yellow Group 13B.
*Persistence.*—The berries commonly are retained on the plant unit April at Jennersville, Pa., U.S.A.
*Seeds.*—Quantity: One per fruit.
*Shape.*—Oval.
*Length.*—Approximately 5 mm on average.
*Diameter.*—Approximately 3 mm on average.
*Color.*—Golden yellow, Yellow-Orange Group 22A.

Plants of the new cultivar have been found to tolerate temperatures as low as −10° F.

The new cultivar has been found to grow well in containers under commercial growing conditions. A softwood cutting commonly roots in approximately 25 days at 32 ° C. A rooted liner commonly is formed in approximately 65 days at 32° C., and a finished plant commonly is produced in one growing season when grown in a one-gallon container.

Under commercial growing conditions during observations to date plants of the new cultivar have been found to be resistant to pathogens common to *Viburnum*. Also, no particular susceptibility of the plant to damage by insects has been experienced during observations to date.

The new 'Vernon Morris' cultivar has not been observed to date under all possible environmental conditions. Accordingly, it is possible that the phenotype may vary somewhat with variations in the environment, such as temperature, light intensity, day length, and other cultural conditions without variance of the genotype. For instance, leaf coloration may vary with the composition and concentration of the fertilizer that is utilized.

I claim:

1. A new and distinct *Viburnum dilatatum* plant having the following combination of characteristics:

(a) displays an upright and rounded configuration, (b) is freely branching and forms a dense and bushy growth habit, (c) displays attractive medium green foliage that is relatively less susceptible to marginal scorching than other plants of the species, (d) forms numerous small white flowers in large hemispherical cymes, and (e) forms attractive large creamy-yellow fruit that persists late into the spring;

substantially as illustrated and described.

* * * * *